United States Patent
Galabura et al.

(10) Patent No.: US 11,931,468 B2
(45) Date of Patent: Mar. 19, 2024

(54) FEMININE CARE ABSORBENT ARTICLE CONTAINING NANOPOROUS SUPERABSORBENT PARTICLES

(71) Applicant: Kimberly-Clark Worldwide, Inc., Neenah, WI (US)

(72) Inventors: Yuriy Galabura, Appleton, WI (US); Austin N. Pickett, Menasha, WI (US); WanDuk Lee, Appleton, WI (US); Vasily A. Topolkaraev, Appleton, WI (US); Palani Raj R. Wallajapet, Neenah, WI (US); Cynthia S. Krueger, Winneconne, WI (US); Mark M. Mleziva, Appleton, WI (US); Richmond R. Cohen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1099 days.

(21) Appl. No.: 16/631,875

(22) PCT Filed: Jul. 20, 2018

(86) PCT No.: PCT/US2018/043105
§ 371 (c)(1),
(2) Date: Jan. 17, 2020

(87) PCT Pub. No.: WO2019/023065
PCT Pub. Date: Jan. 31, 2019

(65) Prior Publication Data
US 2020/0147258 A1    May 14, 2020

Related U.S. Application Data

(60) Provisional application No. 62/538,000, filed on Jul. 28, 2017.

(51) Int. Cl.
*A61F 13/53* (2006.01)
*A61F 13/537* (2006.01)
(Continued)

(52) U.S. Cl.
CPC ............ *A61L 15/425* (2013.01); *A61F 13/53* (2013.01); *A61F 13/53713* (2013.01);
(Continued)

(58) Field of Classification Search
CPC .. A61F 2013/15463; A61F 2013/15495; A61F 2013/530481; A61F 2013/530489;
(Continued)

(56) References Cited

U.S. PATENT DOCUMENTS

| | | | |
|---|---|---|---|
| 3,957,651 A | 5/1976 | Kesting | |
| 4,057,669 A | 11/1977 | McConnell | |

(Continued)

FOREIGN PATENT DOCUMENTS

| | | |
|---|---|---|
| BR | PI0904295 | 6/2011 |
| CN | 1234407 A | 11/1999 |

(Continued)

OTHER PUBLICATIONS

Buchholz et al., Wily-VCH, Modern Superabsorbent Polymer Technology, 1998.

(Continued)

*Primary Examiner* — Catharine L Anderson
(74) *Attorney, Agent, or Firm* — Dority & Manning, P.A.

(57) ABSTRACT

A feminine care absorbent article comprising an absorbent member positioned between a topsheet and a baffle is provided. The absorbent member contains at least one layer that comprises superabsorbent particles containing nanopores having an average cross-sectional dimension of from about 10 to about 500 nanometers.

22 Claims, 7 Drawing Sheets

(51) Int. Cl.
*A61L 15/12* (2006.01)
*A61L 15/20* (2006.01)
*A61L 15/24* (2006.01)
*A61L 15/42* (2006.01)
*A61L 15/60* (2006.01)
*A61F 13/15* (2006.01)
*A61F 13/534* (2006.01)
*A61F 13/535* (2006.01)

(52) U.S. Cl.
CPC .............. *A61L 15/12* (2013.01); *A61L 15/20* (2013.01); *A61L 15/24* (2013.01); *A61L 15/60* (2013.01); *A61F 2013/15463* (2013.01); *A61F 2013/15495* (2013.01); *A61F 2013/15967* (2013.01); *A61F 2013/16* (2013.01); *A61F 2013/530489* (2013.01); *A61F 2013/530496* (2013.01); *A61F 2013/530569* (2013.01); *A61F 2013/530605* (2013.01); *A61F 2013/5307* (2013.01); *A61F 2013/530715* (2013.01); *A61F 2013/530737* (2013.01); *A61F 2013/5349* (2013.01); *A61F 2013/5355* (2013.01); *A61L 2400/12* (2013.01)

(58) Field of Classification Search
CPC ........ A61F 2013/530569; A61F 2013/530591; A61F 2013/5307; A61F 2013/530708; A61F 2013/530715; A61F 2013/530722; A61F 2013/530729; A61F 2013/530737; A61F 2013/530751; A61F 2013/530766; A61L 15/20; A61L 15/60
See application file for complete search history.

(56) References Cited

U.S. PATENT DOCUMENTS

| | | | |
|---|---|---|---|
| 4,076,663 A | 2/1978 | Masuda et al. | |
| 4,100,324 A | 7/1978 | Anderson et al. | |
| 4,286,082 A | 8/1981 | Tsubakimoto et al. | |
| 4,340,706 A | 7/1982 | Obayashi et al. | |
| 4,497,930 A | 2/1985 | Yamasaki et al. | |
| 4,507,438 A | 3/1985 | Obayashi et al. | |
| 4,654,039 A | 3/1987 | Brandt et al. | |
| 4,666,975 A | 5/1987 | Yamasaki et al. | |
| 4,683,274 A | 7/1987 | Nakamura et al. | |
| 4,704,116 A | 11/1987 | Enloe | |
| 4,798,603 A | 1/1989 | Meyer et al. | |
| 4,801,494 A | 1/1989 | Datta et al. | |
| 4,908,026 A | 3/1990 | Sukiennik et al. | |
| 5,145,906 A | 9/1992 | Chambers et al. | |
| 5,192,606 A | 3/1993 | Oda et al. | |
| 5,248,309 A | 9/1993 | Serbiak et al. | |
| 5,350,624 A | 9/1994 | Georger et al. | |
| 5,405,666 A | 4/1995 | Brindle | |
| 5,415,640 A | 5/1995 | Kirby et al. | |
| 5,486,166 A | 1/1996 | Bishop et al. | |
| 5,490,846 A | 2/1996 | Ellis et al. | |
| 5,494,940 A | 2/1996 | Unger | |
| 5,498,478 A | 3/1996 | Hansen | |
| 5,508,102 A | 4/1996 | Georger et al. | |
| 5,560,878 A | 10/1996 | Dragoo et al. | |
| 5,573,994 A | 11/1996 | Kabra et al. | |
| 5,702,377 A | 12/1997 | Collier et al. | |
| 5,797,894 A * | 8/1998 | Cadieux ................ | A61F 13/539 |
| | | | 604/378 |
| 5,814,673 A | 9/1998 | Khait | |
| 5,888,231 A | 3/1999 | Sandvig et al. | |
| 5,931,823 A | 8/1999 | Stokes et al. | |
| 5,973,014 A | 10/1999 | Funk et al. | |
| 6,019,996 A | 2/2000 | Cheong | |
| 6,060,638 A | 5/2000 | Paul et al. | |
| 6,071,406 A | 6/2000 | Tsou | |
| 6,143,211 A | 11/2000 | Mathiowitz et al. | |
| 6,150,002 A | 11/2000 | Varona | |
| 6,222,091 B1 | 4/2001 | Beihoffer et al. | |
| 6,271,278 B1 * | 8/2001 | Park ................... | C08F 291/00 |
| | | | 521/142 |
| 6,376,618 B1 | 4/2002 | Mitchell et al. | |
| 6,431,477 B1 | 8/2002 | Pallmann | |
| 6,479,003 B1 | 11/2002 | Furgiuele et al. | |
| 6,494,390 B1 | 12/2002 | Khait et al. | |
| 6,573,305 B1 | 6/2003 | Thunhorst et al. | |
| 6,663,611 B2 | 12/2003 | Blaney et al. | |
| 6,689,465 B1 | 2/2004 | Omori et al. | |
| 6,720,073 B2 | 4/2004 | Lange et al. | |
| 6,737,491 B2 | 5/2004 | Soerens et al. | |
| 6,818,173 B1 | 11/2004 | Khait et al. | |
| 6,849,672 B2 | 2/2005 | Mehawej et al. | |
| 6,939,914 B2 | 9/2005 | Qin et al. | |
| 6,960,617 B2 | 11/2005 | Omidian et al. | |
| 7,056,957 B2 | 6/2006 | Omidian et al. | |
| 7,265,192 B2 | 9/2007 | Soerens et al. | |
| 7,288,317 B2 | 10/2007 | Poulin et al. | |
| 7,396,584 B2 | 7/2008 | Azad et al. | |
| 7,510,133 B2 | 3/2009 | Pallmann | |
| 7,777,095 B2 | 8/2010 | Soerens | |
| 7,858,841 B2 * | 12/2010 | Krautkramer ......... | A61F 13/534 |
| | | | 604/367 |
| 7,988,992 B2 | 8/2011 | Omidian et al. | |
| 8,021,998 B2 | 9/2011 | Qin et al. | |
| 8,138,281 B2 | 3/2012 | Weismantel et al. | |
| 8,383,877 B2 | 2/2013 | Singh Kainth et al. | |
| 8,742,023 B2 | 6/2014 | Fujimura et al. | |
| 9,078,946 B2 | 7/2015 | Badri et al. | |
| 10,022,468 B2 * | 7/2018 | Yahiaoui ............... | A61F 13/82 |
| 10,046,305 B2 * | 8/2018 | Kim ..................... | C08J 3/075 |
| 10,138,346 B2 * | 11/2018 | Duong .................. | C08J 9/365 |
| 2002/0187302 A1 | 12/2002 | Koslow | |
| 2003/0003830 A1 | 1/2003 | Ouederni et al. | |
| 2003/0130639 A1 | 7/2003 | Ishikawa et al. | |
| 2003/0200991 A1 | 10/2003 | Keck et al. | |
| 2004/0019166 A1 | 1/2004 | Soerens et al. | |
| 2004/0067214 A1 | 4/2004 | Krautkramer et al. | |
| 2004/0092658 A1 | 5/2004 | Qin et al. | |
| 2004/0102750 A1 | 5/2004 | Jameson | |
| 2005/0054255 A1 | 3/2005 | Morman et al. | |
| 2005/0059941 A1 | 3/2005 | Baldwin et al. | |
| 2005/0288641 A1 | 12/2005 | Sorens | |
| 2006/0167424 A1 * | 7/2006 | Chang ................ | A61F 13/15203 |
| | | | 604/378 |
| 2006/0178465 A9 | 8/2006 | Torkelson et al. | |
| 2007/0049153 A1 | 3/2007 | Dunbar et al. | |
| 2007/0049888 A1 | 3/2007 | Soerens et al. | |
| 2008/0058747 A1 | 3/2008 | Singh et al. | |
| 2008/0227944 A1 | 9/2008 | Ambrosio et al. | |
| 2010/0261812 A1 | 10/2010 | Qin et al. | |
| 2010/0266794 A1 | 10/2010 | Wright et al. | |
| 2011/0301560 A1 | 12/2011 | Fujimura et al. | |
| 2012/0219728 A1 | 8/2012 | Badri et al. | |
| 2013/0030340 A1 | 1/2013 | Vincent et al. | |
| 2013/0037481 A1 | 2/2013 | Lalouch et al. | |
| 2013/0172509 A1 | 7/2013 | Pawloski et al. | |
| 2014/0296507 A1 | 10/2014 | Sannino et al. | |
| 2014/0309607 A1 | 10/2014 | Richlen et al. | |
| 2015/0342799 A1 | 12/2015 | Michiels et al. | |
| 2016/0168349 A1 | 6/2016 | Topolkaraev et al. | |
| 2016/0175811 A1 * | 6/2016 | Behabtu ............... | C08B 37/0009 |
| | | | 435/97 |
| 2016/0354757 A1 | 12/2016 | Lee et al. | |
| 2017/0079854 A1 | 3/2017 | Butler et al. | |
| 2017/0216817 A1 | 8/2017 | Torii et al. | |
| 2018/0043332 A1 | 2/2018 | Lee et al. | |
| 2018/0194904 A1 | 7/2018 | Lee et al. | |

FOREIGN PATENT DOCUMENTS

| | | |
|---|---|---|
| CN | 104107681 | 10/2014 |
| CN | 104974312 A | 10/2015 |
| EP | 1178843 | 2/2002 |
| EP | 2740747 | 6/2014 |
| EP | 3321308 A1 | 5/2018 |

(56) References Cited

FOREIGN PATENT DOCUMENTS

| | | |
|---|---|---|
| GB | 11020342 | 2/1968 |
| GB | 1174959 | 12/1969 |
| JP | H01292003 | 11/1989 |
| JP | H02194010 | 7/1990 |
| JP | H0364301 | 3/1991 |
| JP | 2006342306 | 12/2006 |
| JP | 2013252330 | 12/2013 |
| JP | 2013252331 | 12/2013 |
| KR | 100947302 | 3/2010 |
| KR | 2017/0066480 A | 6/2017 |
| KR | 1020170063818 | 6/2017 |
| KR | 1020170075624 | 7/2017 |
| KR | 1020170075643 | 7/2017 |
| RU | 2010138539 | 3/2012 |
| WO | WO9512632 | 5/1995 |
| WO | WO2005063313 | 7/2005 |
| WO | WO2009022358 | 2/2009 |
| WO | WO2011063372 | 5/2011 |

OTHER PUBLICATIONS

International Search Report and Written Opinion for PCT/US2018/043105 dated Oct. 31, 2018, 10 pages.

Third Party Observation for PCT/US2018/043105 dated Nov. 21, 2019, 10 pages.

Udoh et al., "Microporous Polymer Particles via Phase Inversion in Microfluidics: Impact of Nonsolvent Quality", American Chemical Society, Langmuir Jul. 22, 2016, 32 (32), pp. 8131-8140.

Korean Office Action Corresponding to Application No. 1020207003778 dated Mar. 9, 2021.

Chinese Office Action Corresponding to Application No. 201880049788 dated Jul. 30, 2021.

Great Britain Office Action Corresponding to Application No. 2001615 dated Jun. 10, 2021.

Great Britain Office Action Corresponding to Application No. 2001615 dated Nov. 18, 2015.

* cited by examiner

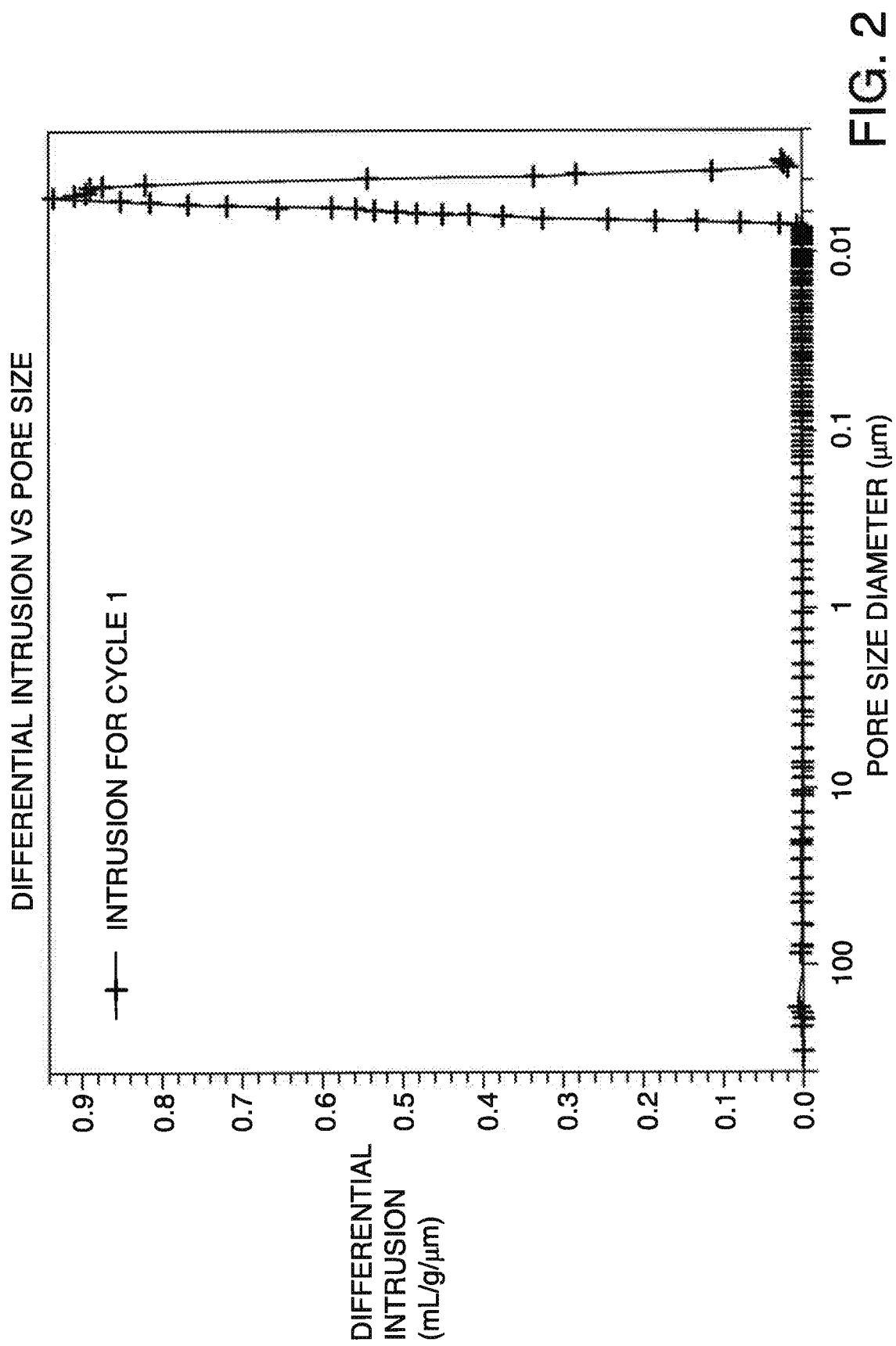

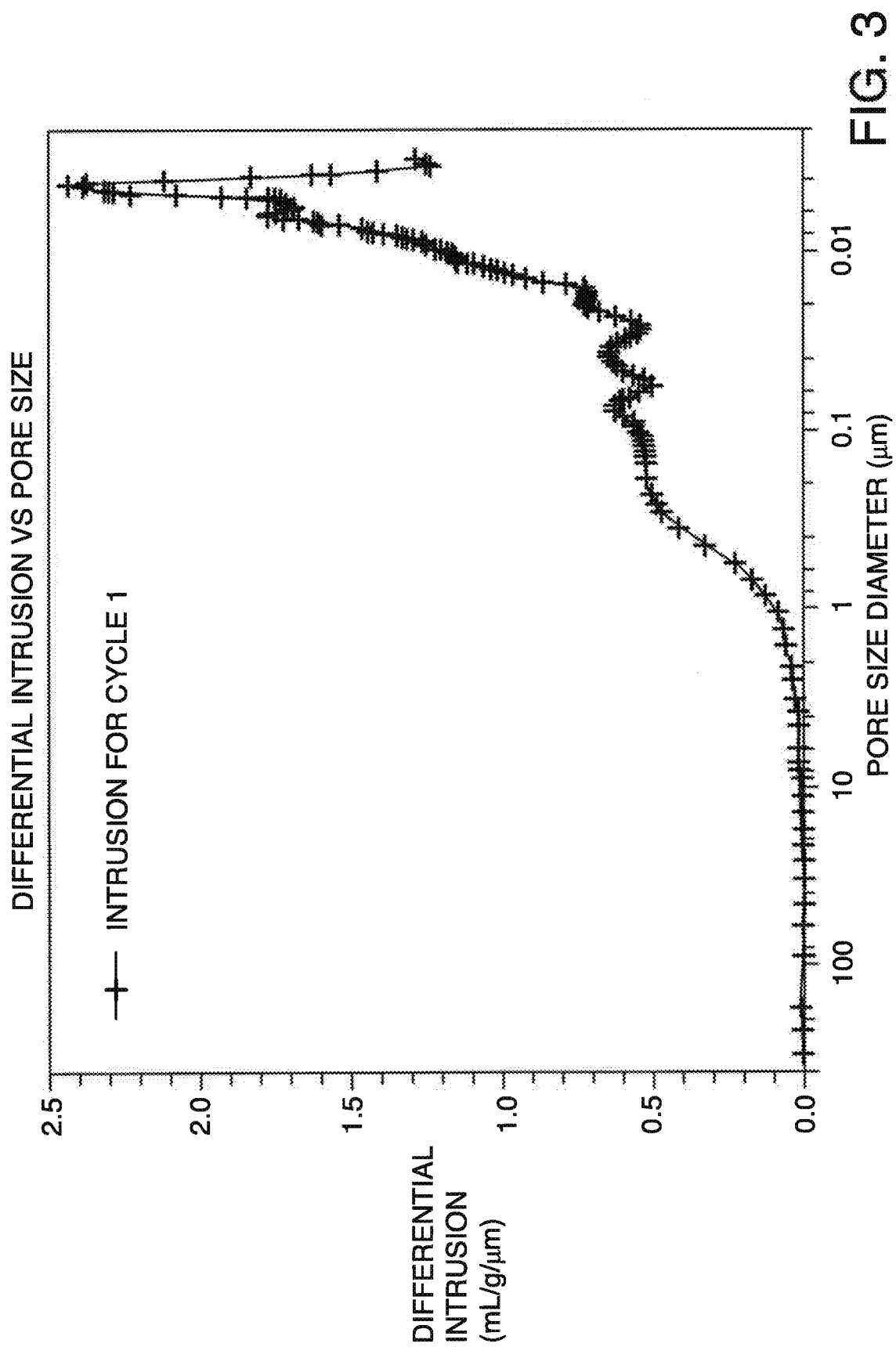

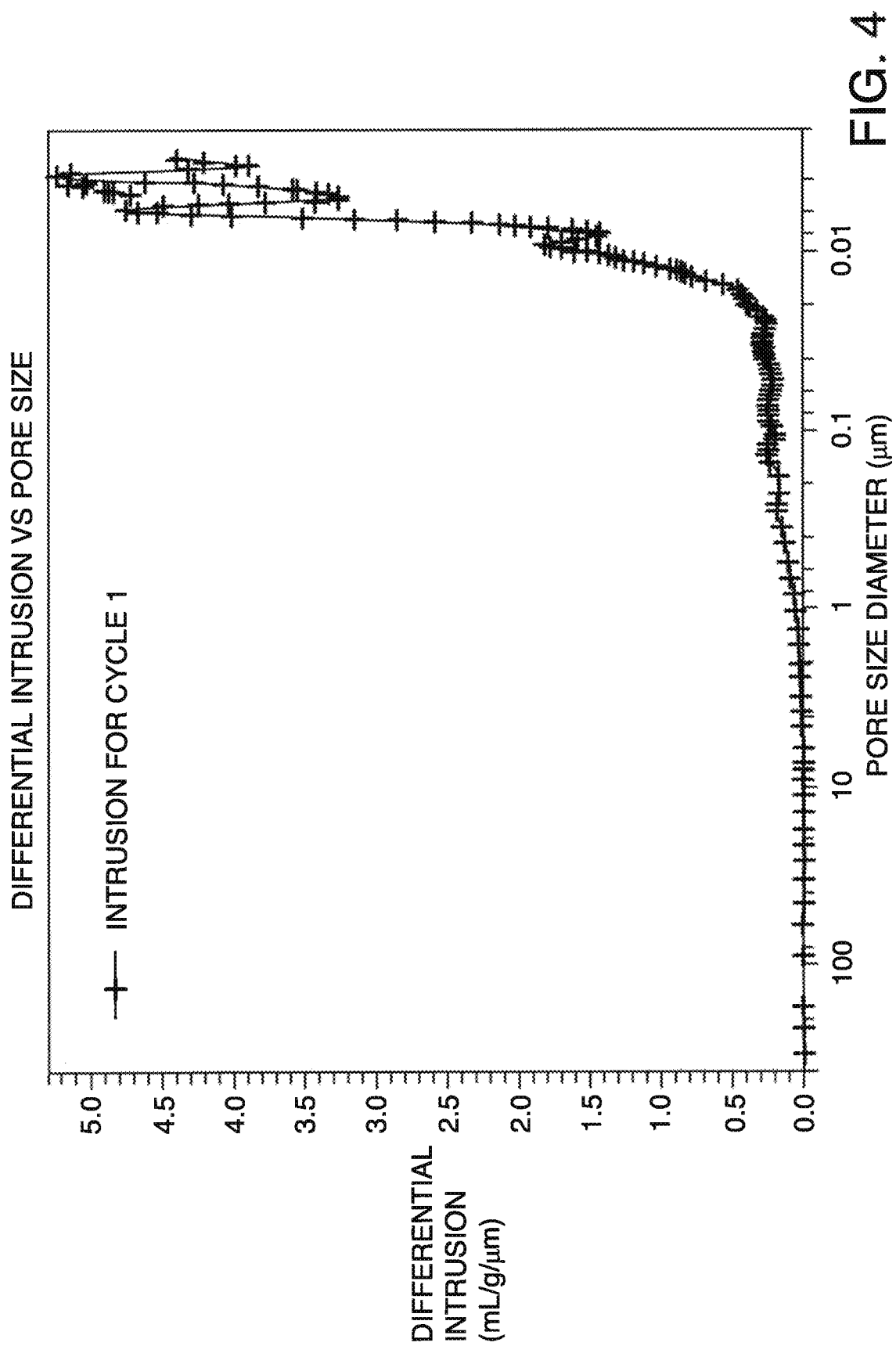

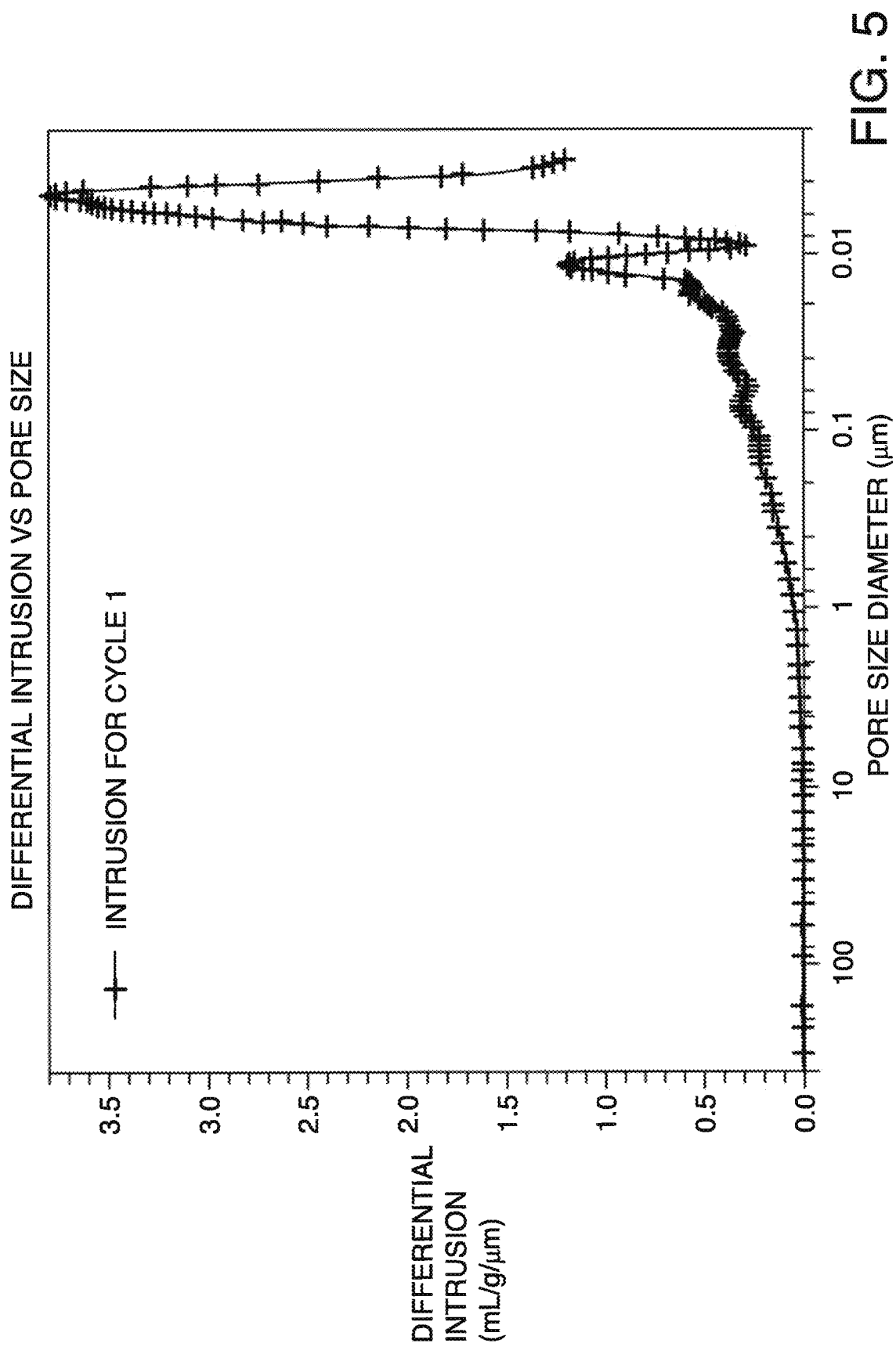

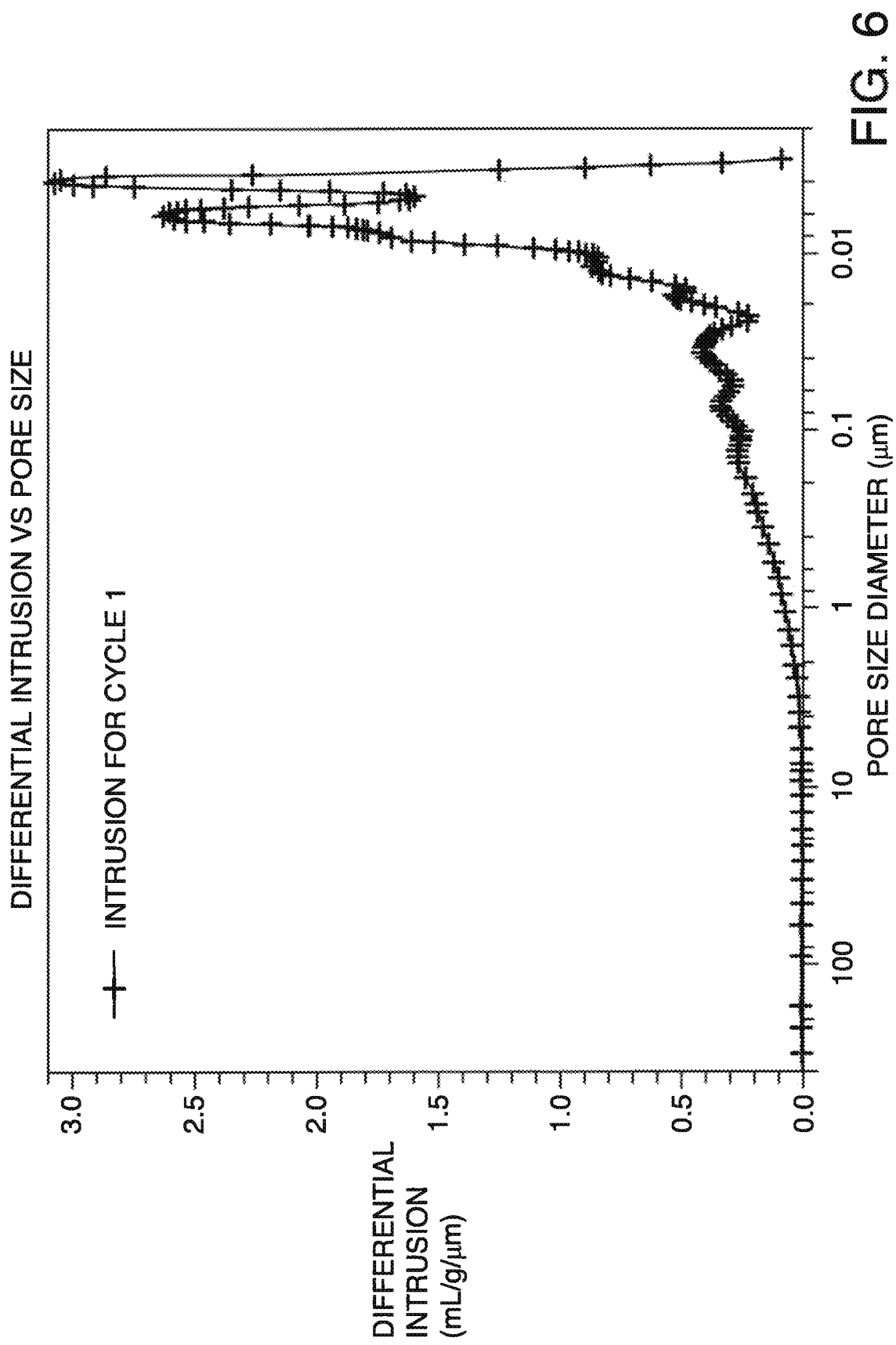

FEMININE CARE ABSORBENT ARTICLE CONTAINING NANOPOROUS SUPERABSORBENT PARTICLES

RELATED APPLICATIONS

The present application is the national stage entry of International Patent Application No. PCT/US2018/043105 having a filing date of Jul. 20, 2018, which claims priority to U.S. Provisional Application Ser. No. 62/538,000 having a filing date of Jul. 28, 2017, both of which are incorporated herein in their entirety by reference thereto.

BACKGROUND OF THE INVENTION

Feminine care absorbent articles (e.g., sanitary napkins, pads, etc.) typically include an absorbent member, such as an absorbent core, which contains a combination of hydrophilic fibers and superabsorbent particles. While such absorbent members have a high degree of absorbent capacity, they can sometimes leak during use. The leakage may be due in part to the intake rate of the structure, which is the rate at which a liquid is taken into and entrained within the structure. More particularly, the intake rate may decrease due to an insufficient absorption rate of the superabsorbent particles. Further, as the particles swell upon absorption of menses, the open channels within the particles and/or between the particles and the hydrophilic fibers can become blocked. As such, a need currently exists for feminine care absorbent articles having improved performance.

SUMMARY OF THE INVENTION

In accordance with one embodiment of the present invention, a feminine care absorbent article is disclosed that comprises an absorbent member positioned between a topsheet and a baffle. The absorbent member contains at least one layer that comprises superabsorbent particles that contain nanopores having an average cross-sectional dimension of from about 10 to about 500 nanometers.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 2 shows the pore size distribution of the control particles referenced in Example 1 prior to solvent exchange;

FIG. 3 shows the pore size distribution of the particles of Example 1 after solvent exchange with methanol;

FIG. 4 shows the pore size distribution of the particles of Example 2 after solvent exchange with ethanol;

FIG. 5 shows the pore size distribution of the particles of Example 3 after solvent exchange with isopropyl alcohol;

FIG. 6 shows the pore size distribution of the particles of Example 4 after solvent exchange with acetone.

Figure 1A:
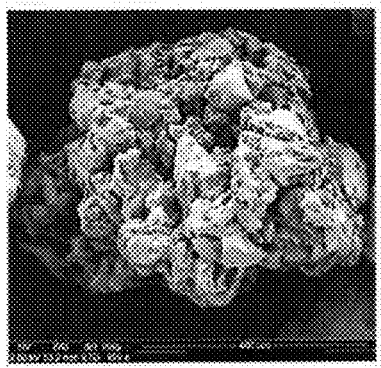
FIG. 1 shows SEM microphotographs of the superabsorbent particles of Example 1, wherein FIG. 1A (456×), FIG. 1B (10,000×, fractured), and FIG. 1C (55,000×, fractured) show the particles prior to pore formation and FIG. 1D (670×), FIG. 1E (10,000×, fractured) and FIG. 1F (55,000×, fractured) show the particles after pore formation.
Figure 1B:
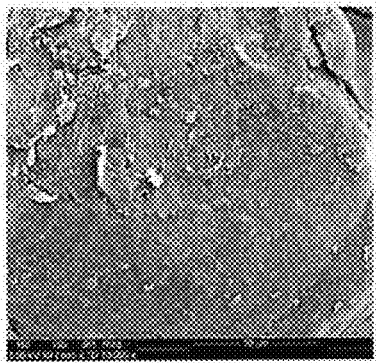
Figure 1C:
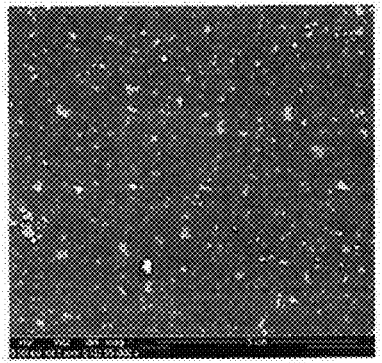
Figure 1D:
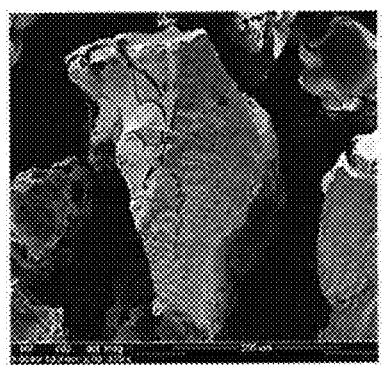
Figure 1E:
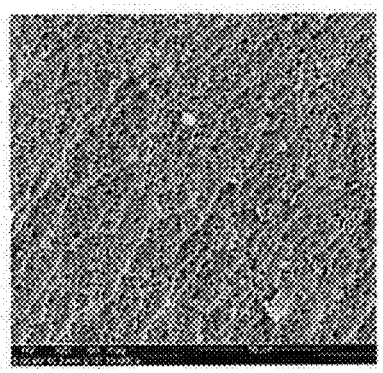
Figure 1F:
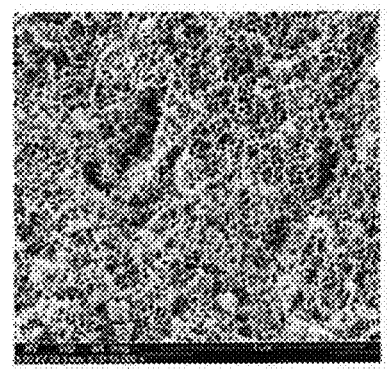

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a feminine care absorbent article, such as a sanitary napkin, pad, tampon, etc., which contains a topsheet, baffle, and an absorbent member positioned between the topsheet and the baffle. The absorbent member contains a plurality of superabsorbent particles, which typically have a median size (e.g., diameter) of from about 50 to about 2,000 micrometers, in some embodiments from about 100 to about 1,000 micrometers, and in some embodiments, from about 200 to about 700 micrometers. The term "median" size as used herein refers to the "D50" size distribution of the particles, which means that at least 50% of the particles have the size indicated. The particles may likewise have a D90 size distribution (at least 90% of the particles have the size indicated) within the ranges noted above. The diameter of particles may be determined using known techniques, such as by ultracentrifuge, laser diffraction, etc. For example, particle size distribution can be determined according to a standard testing method such as ISO 13320:2009. The particles may also possess any desired shape, such as flake, nodular, spherical, tube, etc. The size of the particles may be controlled to optimize performance for a particular application. The specific surface area of the particles may also be relatively large, such as about 0.2 square meters per gram ($m^2/g$) or more, in some embodiments about 0.6 $m^2/g$ or more, and in some embodiments, from about 1 $m^2/g$ to about 5 $m^2/g$, such as determined in accordance with the B.E.T. test method as described in ISO 9277:2010.

Regardless of their particular size or shape, the superabsorbent particles are porous in nature and generally possess a porous network, which may contain a combination of closed and open-celled pores. The total porosity of the particles may be relatively high. For example, the particles may exhibit a total pore area of about 2 square meters per gram ($m^2/g$) or more, in some embodiments from about 5 to about 150 $m^2/g$, and in some embodiments, from about 15 to about 60 $m^2/g$. The percent porosity may also be about 5% or more, in some embodiments from about 10% to about 60%, and in some embodiments, from about 15% to about 40%. Another parameter that is characteristic of porosity is bulk density. In this regard, the bulk density of the superabsorbent particles of the present invention may, for example, be less than about 0.7 grams per cubic centimeter ($g/cm^3$), in some embodiments from about 0.1 to about 0.65 g/cm$^3$, and in some embodiments, from about 0.2 to about 0.6 g/cm$^3$, as determined at a pressure of 0.58 psi via mercury intrusion.

To achieve the desired pore properties, the porous network contains a plurality of nanopores having an average cross-sectional dimension (e.g., width or diameter) of from about 10 to about 500 nanometers, in some embodiments from about 15 to about 450 nanometers, and in some embodiments, from about 20 to about 400 nanometers. The term "cross-sectional dimension" generally refers to a characteristic dimension (e.g., width or diameter) of a pore, which is substantially orthogonal to its major axis (e.g., length). It should be understood that multiple types of pores may exist within the network. For example, micropores may also be formed that have an average cross-sectional dimension of from about 0.5 to about 30 micrometers, in some embodiments from about 1 to about 20 micrometers, and in some embodiments, from about 2 micrometers to about 15 micrometers. Nevertheless, nanopores can be present in a relatively high amount in the network. For example, the nanopores may constitute at least about 25 vol. %, in some embodiments at least about 40 vol. %, and in some embodiments, from about 40 vol. % to 80 vol. % of the total pore volume of the particles. The average percent volume occupied by the nanopores within a given unit volume of the material may also be from about 15% to about 80% per cm$^3$, in some embodiments from about 20% to about 70%, and in some embodiments, from about 30% to about 60% per cubic centimeter of the particles. Multiple subtypes of nanopores may also be employed. In certain embodiments, for instance, first nanopores may be formed that have an average cross-sectional dimension of from about 80 to about 500 nanometers, in some embodiments from about 90 to about 450 nanometers, and in some embodiments, from about 100 to about 400 nanometers, while second nanopores may be formed that have an average cross-sectional dimension of from about 1 to about 80 nanometers, in some embodiments from about 5 to about 70 nanometers, and in some embodiments from about 10 to about 60 nanometers. The nanopores may have any regular or irregular shape, such as spherical, elongated, etc. Regardless, the average diameter of the pores within the porous network will typically be from about 1 to about 1,200 nanometers, in some embodiments from about 10 nanometers to about 1,000 nanometers, in some embodiments from about 50 to about 800 nanometers, and in some embodiments, from about 100 to about 600 nanometers.

Due in part to the particular nature of the porous network, the present inventors have discovered that the resulting superabsorbent particles can exhibit an enhanced rate of absorption during the specific time period in which they begin to contact a bodily fluid, such as menses. This increased rate can be characterized in a variety of ways. For example, the particles may exhibit a low Vortex Time, which refers to the amount of time in seconds required for an amount of the superabsorbent particles to close a vortex created by stirring a menses simulant (e.g., defibrinated swine blood having a hematocrit level of 35 vol. %) according to the test described below. More particularly, the superabsorbent particles may exhibit a Vortex Time of about 80 seconds or less, in some embodiments about 70 seconds or less, in some embodiments about 65 seconds or less, in some embodiments about 60 seconds or less, in some embodiments about 50 seconds or less, and in some embodiments, from about 0.5 to about 40 seconds. Alternatively, after being placed into contact with a menses simulant for 1.8 kiloseconds ("ks"), the Saturation Rate of the particles may be about 7 g/g/ks or more, in some embodiments about 8 g/g/ks or more, in some embodiments about 10 g/g/ks or more, and in some embodiments, from about 12 to about 50 g/g/ks.

Notably, the increased rate of absorption can be maintained without sacrificing the absorbent capacity of the particles. For example, the Absorbent Capacity (at 0.5 psi) of the particles may be about 15 g/g or more, in some embodiments about 18 g/g or more, and in some embodiments, from about 20 to about 60 g/g. Likewise, the particles may exhibit a Centrifuge Retention Capacity ("CRC") of about 20 grams menses simulant per gram of superabsorbent particles (g/g) or more, in some embodiments about 20 g/g or more, and in some embodiments, from about 25 to about 60 g/g.

Yet another benefit of the particles is that the pore structure is reversible during use of the absorbent article. That is, when the absorbent member is placed in contact with menses, the superabsorbent particles may absorb the menses and swell until the porous network collapses. In this manner, the swollen particles are converted into relatively solid particles, which may increase the open channels between superabsorbent particles, or between the particles and the fibrous material within the absorbent member, thereby minimizing any gel blocking that might occur.

Various embodiments of the present invention will now be described in more detail.

I. Superabsorbent Particles

The superabsorbent particles are generally formed from a three-dimensional crosslinked polymer network that contains repeating units derived from one or more ethylenically (e.g., monoethylenically) unsaturated monomeric compounds having at least one hydrophilic radical, such as a carboxyl, carboxylic acid anhydride, carboxylic acid salt, sulfonic acid, sulfonic acid salt, hydroxyl, ether, amide, amino, or quaternary ammonium salt group. Particular examples of suitable ethylenically unsaturated monomeric compounds for forming the superabsorbent particles include, for instance, carboxylic acids (e.g., (meth)acrylic acid (encompasses acrylic acid and/or methacrylic acid), maleic acid, fumaric acid, crotonic acid, sorbic acid, itaconic acid, cinnamic acid, etc.); carboxylic acid anhydrides (e.g., maleic anhydride); salts (alkali metal salts, ammonium salts, amine salts, etc.) of carboxylic acids (e.g., sodium (meth) acrylate, trimethylamine(meth)acrylate, triethanolamine-(meth)acrylate, sodium maleate, methylamine maleate, etc.); vinyl sulfonic acids (e.g., vinylsulfonic acid, allyl sulfonic acid, vinyltoluenesulfonic acid, styrene sulfonic acid, etc.); (meth)acrylic sulfonic acids (e.g., sulfopropyl (meth)acrylate, 2-hydroxy-3-(meth)acryloxy propyl sulfonic acid, etc.); salts of vinyl sulfonic acids or (meth)acrylic sulfonic acids; alcohols (e.g., (meth)allyl alcohol); ethers or esters of polyols (e.g., hydroxyethyl (meth)acrylate, hydroxypropyl (meth)acrylate, triethylene glycol (meth)acrylate, poly(oxyethylene oxypropylene) glycol mono (meth)allyl ether (in which hydroxyl groups may be etherified or esterified), etc.); vinylformamides; (meth)acrylamides, N-alkyl (meth)acrylamides (e.g., N-methylacrylamide, N-hexylacrylamide, etc.), N,N-dialkyl (meth)acrylamides (e.g., N,N-dimethylacrylamide, N,N-di-n-propylacrylamide, etc.); N-hydroxyalkyl (meth)acrylamides (e.g., N-methylol(meth)acrylamide, N-hydroxyethyl-(meth)acrylamide, etc.); N,N-dihydroxyalkyl (meth)acrylamides (e.g., N,N-dihydroxyethyl(meth)acrylamide); vinyl lactams (e.g., N-vinylpyrrolidone); amino group-containing esters (e.g., dialkylaminoalkyl esters, dihydroxyalkylaminoalkyl esters, morpholinoalkyl esters, etc.) of carboxylic acids (e.g., dimethylaminoethyl (meth)acrylate, diethylaminoethyl (meth)

acrylate, morpholinoethyl (meth)acrylate, dimethylaminoethyl fumarate, etc.); heterocyclic vinyl compounds (e.g., 2-vinyl pyridine, 4-vinyl pyridine, N-vinyl pyridine, N-vinyl imidazole), etc.); quaternary ammonium salt group-containing monomers (e.g., N,N,N-trimethyl-N-(meth)acryloyloxyethylammonium chloride, N,N,N-triethyl-N-(meth)acryloyloxyethylammonium chloride, 2-hydroxy-3-(meth)acryloyloxypropyl trimethyl ammonium chloride, etc.); and so forth, as well as combinations of any of the foregoing. In most embodiments, (meth)acrylic acid monomeric compounds, as well as salts thereof, are employed to form the superabsorbent particles.

The monomeric compounds referenced above are generally soluble in water. It should be understood, however, that compounds may also be employed that can become water-soluble through hydrolysis. Suitable hydrolyzable monomers may include, for instance, ethylenically unsaturated compounds having at least one hydrolyzable radical, such as esters, amide and nitrile groups. Particular examples of such hydrolysable monomers include methyl (meth)acrylate, ethyl (meth)acrylate, 2-ethylhexyl (meth)acrylate, vinyl acetate, (meth)allyl acetate, (meth)acrylonitrile, etc. Furthermore, it should be understood that additional monomers may be employed so that the resulting particles are formed as a copolymer, such as a random, grafted, or block copolymer. If desired, the comonomer(s) may be selected from the group of monomers listed above. For instance, the comonomer(s) may be (meth)acrylic acid, salt of (meth)acrylic acid, maleic acid anhydride, etc. In one particular embodiment, for example, a copolymer may be formed from acrylic acid (or a salt thereof) and maleic anhydride. In other embodiments, as described in more detail below, a comonomer may also be employed that contains a crosslinkable functionality, such as an alkoxysilane. Regardless of the comonomer(s) employed, it is generally desired that the primary ethylenically unsaturated monomer(s) constitute at least about 50 mol. %, in some embodiments from about 55 mol. % to about 99 mol. %, and in some embodiments, from about 60 mol. % to about 98 mol. % of the monomers used to form the polymer, while comonomer(s) constitute no more than about 60 mol. %, in some embodiments from about 1 mol. % to about 50 mol. %, and in some embodiments, from about 2 mol. % to about 40 mol. % of the monomers used to form the polymer.

To form a network capable of absorbing menses, it is generally desired that the polymer is crosslinked during and/or after polymerization. In one embodiment, for instance, the ethylenically unsaturated monomeric compound(s) may be polymerized in the presence of a crosslinking agent to provide a crosslinked polymer. Suitable crosslinking agents typically possess two or more groups that are capable of reacting with the ethylenically unsaturated monomeric compound and that are at least partially water soluble or water dispersible, or at least partially soluble or dispersible in an aqueous monomer mixture. Examples of suitable crosslinking agents may include, for instance, tetraallyloxyethane, N,N'-methylene bisacrylamide, N,N'-methylene bismethacrylamide, triallylamine, trimethylol propane triacrylate, glycerol propoxy triacrylate, divinylbenzene, N-methylol acrylamide, N-methylol methacrylamide, glycidyl methacrylate, polyethylene polyamines, ethyl diamine, ethyl glycol, glycerin, tetraallyloxyethane and triallyl ethers of pentaerythritol, aluminates, silica, alumosilicates, etc., as well as combinations thereof. The amount of the crosslinking agent may vary, but is typically present in an amount of from about 0.005 to about 1.0 mole percent based on moles of the ethylenically unsaturated monomeric compound(s).

In the embodiments described above, crosslinking generally occurs during polymerization. In other embodiments, however, the polymer may contain a latent functionality that is capable of becoming crosslinked when desired. For instance, the polymer may contain an alkoxysilane functionality which, upon exposure to water, forms a silanol functional group that condenses to form a crosslinked polymer. One particular example of such a functionality is a trialkoxysilane having the following general structure:

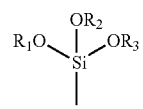

wherein $R_1$, $R_2$ and $R_3$ are alkyl groups independently having from 1 to 6 carbon atoms.

To introduce such a functionality into the polymer structure, a monomeric compound may be employed that contains the functionality, such as an ethylenically unsaturated monomer containing a trialkoxysilane functional group. Particularly suitable monomers are (meth)acrylic acids or salts thereof, such as methacryloxypropyl trimethoxysilane, methacryloxyethyl trimethoxysilane, methacryloxypropyl triethoxysilane, methacryloxypropyl tripropoxysilane, acryloxypropylmethyl dimethoxysilane, 3-acryloxypropyl trimethoxysilane, 3-methacryloxypropylmethyl diethoxysilane, 3-methacryloxypropylmethyl dimethoxysilane, 3-methacryloxypropyl tris(methoxyethoxy)silane, and so forth. In addition to monomers capable of co-polymerization that contain a trialkoxysilane functional group, it is also possible to use a monomer capable of co-polymerization that can subsequently be reacted with a compound containing a trialkoxysilane functional group or a moiety that reacts with water to form a silanol group. Such a monomer may contain, but is not limited to, an amine or an alcohol. An amine group incorporated into the co-polymer may subsequently be reacted with, for example, but not limited to, (3-chloropropyl)trimethoxysilane. An alcohol group incorporated into the co-polymer may subsequently be reacted with, for example, but not limited to, tetramethoxysilane.

The superabsorbent polymer particles of the present invention may be prepared by any known polymerization method. For instance, the particles may be prepared by any suitable bulk polymerization technique, such as solution polymerization, inverse suspension polymerization, or emulsion polymerization, such as described in U.S. Pat. Nos. 4,076,663, 4,286,082, 4,340,706, 4,497,930, 4,507,438, 4,654,039, 4,666,975, 4,683,274, or 5,145,906. In solution polymerization, for instance, the monomer(s) are polymerized in an aqueous solution. In inverse suspension polymerization, the monomers(s) are dispersed in an alicyclic or aliphatic hydrocarbon suspension medium in the presence of a dispersing agent, such as a surfactant or protective colloid. If desired, the polymerization reaction may be conducted in the presence of a free radical initiator, redox initiator (reducing and oxidizing agents), thermal initiator, photoinitiator, etc. Examples of suitable reducing agents may include, for instance, ascorbic acid, alkali metal sulfites, alkali metal bisulfites, ammonium sulfite, ammonium bisulfite, alkali metal hydrogen sulfite, ammonium hydrogen sulfite, ferrous metal salts, e.g., ferrous sulfates, sugars, aldehydes, primary and secondary alcohols, etc.

Examples of suitable oxidizing agents may include, for instance, hydrogen peroxide, caprylyl peroxide, benzoyl peroxide, cumene peroxide, tertiary butyl diperphthalate, tertiary butyl perbenzoate, sodium percarbonate, sodium peracetate, alkali metal persulfates, ammonium persulfates, alkylhydroperoxides, peresters, diacryl peroxides, silver salts, etc.

If desired, the resulting particles may also be downsized to achieve the desired size noted above. For instance, impact downsizing, which typically employs a grinder having a rotating grinding element, may be used to form the particles. Repeated impact and/or shear stress can be created between the rotating grinding element and a stationary or counter-rotating grinding element. Impact downsizing may also employ air flow to carry and collide the material into a grinding disk (or other shearing element). One particularly suitable impact downsizing apparatus is available commercially from Pallmann Industries (Clifton, N.J.) under the name Turbofiner®, type PLM. In this apparatus, a high activity air whirl is created within a cylindrical grinding chamber between a stationary grinding element and a rotating grinding element of an impact grinding mill. Due to the high air volume, the particles can be impacted and become downsized into the desired particle size. Other suitable impact downsizing processes may be described in U.S. Pat. Nos. 6,431,477 and 7,510,133, both to Pallmann. Another suitable microparticle formation process is cold extrusion downsizing, which generally employs shear and compression forces to form particles having the desired size. For example, the material can be forced through a die at temperatures below the melting point of the matrix polymer. Solid-state shear pulverization is another suitable process that can be used. Such processes generally involve continuous extrusion of the material under high shear and compression conditions while the extruder barrels and a screw are cooled to prevent polymer melting. Examples of such solid state pulverization techniques are described, for instance, in U.S. Pat. No. 5,814,673 to Khait; U.S. Pat. No. 6,479,003 to Furqiuele, et al.; U.S. Pat. No. 6,494,390 to Khait, et al.; U.S. Pat. No. 6,818,173 to Khait; and U.S. Publication No. 2006/0178465 to Torkelson, et al. Yet another suitable microparticle formation technique is known as cryogenic disk milling. Cryogenic disk milling generally employs a liquid (e.g., liquid nitrogen) to cool or freeze the material prior to and/or during grinding. In one embodiment, a single-runner disk milling apparatus can be employed that has a stationary disk and a rotating disk. The material enters between the discs via a channel near the disk center and is formed into particles through the frictional forces created between the discs. One suitable cryogenic disk milling apparatus is available under the name Wedco® cryogenic grinding system from ICO Polymers (Allentown, Pa.).

Although by no means required, additional components may also be combined with the superabsorbent polymer, before, during, or after polymerization. In one embodiment, for instance, high aspect ratio inclusions (e.g., fibers, tubes, platelets, wires, etc.) may be employed to help produce an internal interlocking reinforcing framework that stabilizes the swelling superabsorbent polymer and improves its resiliency. The aspect ratio (average length divided by median width) to may, for instance, range from about 1 to about 50, in some embodiments from about 2 to about 20, and in some embodiments, from about 4 to about 15. Such inclusions may have a median width (e.g., diameter) of from about 1 to about 35 micrometers, in some embodiments from about 2 to about 20 micrometers, in some embodiments from about 3 to about 15 micrometers, and in some embodiments, from about 7 to about 12 micrometers, as well as a volume average length of from about 1 to about 200 micrometers, in some embodiments from about 2 to about 150 micrometers, in some embodiments from about 5 to about 100 micrometers, and in some embodiments, from about 10 to about 50 micrometers. Examples of such high aspect inclusions may include high aspect ratio fibers (also known as "whiskers") that are derived from carbides (e.g., silicon carbide), silicates (e.g., wollastonite), etc.

If desired, a hydrophobic substance may also be combined with the superabsorbent polymer, such as a substance containing a hydrocarbon group, a substance containing a hydrocarbon group having a fluorine atom, a substance having a polysiloxane structure, etc. Examples of such substances as well as superabsorbent particles formed therefrom are described, for instance, in U.S. Pat. No. 8,742,023 to Fuiimura, et al., which is incorporated herein in its entirety by reference thereto. For instance, suitable hydrophobic substances may include polyolefin resins, polystyrene resins, waxes, long-chain fatty acid esters, long-chain fatty acids and salts thereof, long-chain aliphatic alcohols, long-chain aliphatic amides, etc., as well as mixtures thereof. In one particular embodiment, a long-chain fatty acid ester may be employed that is an ester of a fatty acid having 8 to 30 carbon atoms and an alcohol having 1 to 12 carbon atoms, such as methyl laurate, ethyl laurate, methyl stearate, ethyl stearate, methyl oleate, ethyl oleate, glycerol monolaurate, glycerol monostearate, glycerol monooleate, pentaerythritol monolaurate, pentaerythritol monostearate, pentaerythritol monooleate, sorbitol monolaurate, sorbitol monostearate, sorbitol monooleate, sucrose monopalmitate, sucrose dipalmitate, sucrose tripalmitate, sucrose monostearate, sucrose distearate, sucrose tristearate, tallow, etc. In another embodiment, a long-chain fatty acid or a salt thereof may be employed that contains 8 to 30 carbon atoms, such as lauric acid, palmitic acid, stearic acid, oleic acid, dimer acid, behenic acid, etc., as well as zinc, calcium, magnesium, and/or aluminum salts thereof, such as calcium palmitate, aluminum palmitate, calcium stearate, magnesium stearate, aluminum stearate, etc.

Regardless of the specific manner in which the particles are formed, a variety of different techniques can be employed to initiate the creation of the desired porous network. In certain embodiments, control over the polymerization process itself can lead to the formation of pores within the resulting particles. For instance, polymerization may be conducted in heterogeneous, two phase or multiphase systems, with a monomer-rich continuous phase suspended in a solvent-rich minority phase. As the monomer-rich phase begins to polymerize, pore formation can be induced by the solvent-rich phase. Of course, techniques may also be employed in which a porous network is formed within preformed particles. In one particular embodiment, for instance, a technique known as "phase inversion" may be employed in which a polymer dissolved or swollen in a continuous phase solvent system inverts into a continuous phase solid macromolecular network formed by the polymer. This inversion can be induced through several methods, such as by removal of the solvent via a dry process (e.g., evaporation or sublimation), addition of a non-solvent or addition to a non-solvent via a wet process. In dry processes, for example, the temperature (or the pressure) of the particles can be altered so that the solvent system (e.g., water) can be transformed to another state of matter that can be removed without excessive shrinkage, either by evacuating or purging with a gas. Freeze drying, for instance, involves cooling the solvent system below its freezing point and then allowing it to sublime under reduced pressure so that pores are formed. Supercritical drying, on the other hand, involves heating the solvent system under pressure above the supercritical point so that pores are formed.

Wet processes, however, are particularly suitable in that they do not rely on a substantial degree of energy to achieve the desired inversion. In a wet process, the superabsorbent polymer and solvent system may be provided in the form of a single phase homogenous composition. The concentration of the polymer typically ranges from about 0.1% to about 20% wt./vol., and in some embodiments, from about 0.5% to about 10% wt./vol. of the composition. The composition is thereafter contacted with a non-solvent system using any known technique, such as by immersing into a bath, countercurrent washing, spray washing, belt spray, and filtering. The difference in chemical potential between the solvent and non-solvent systems causes molecules of the solvent to diffuse out of the superabsorbent polymer, while molecules of the non-solvent diffuse into the polymer. Ultimately, this causes the polymer composition to undergo a transition from a single phase homogeneous composition to an unstable two phase mixture containing polymer-rich and polymer-poor fractions. Micellar droplets of the non-solvent system in the polymer-rich phase also serve as nucleation sites and become coated with polymer, and at a certain point, these droplets precipitate to form a continuous polymer network. The solvent composition inside the polymer matrix also collapses on itself and forms voids. The matrix can then be dried to remove the solvent and non-solvent systems and form stabile porous particles.

The exact solvent and non-solvent systems employed to accomplish the phase inversion are not particularly critical, so long they are selected in tandem based on their miscibility. More particularly, the solvent and non-solvent systems can be selected so that they have a specific difference in their Hildebrand solubility parameters, $\delta$, which is a predictive indicator of the miscibility of two liquids with higher values generally representing a more hydrophilic liquid and lower values representing a more hydrophobic liquid. It is generally desired that the difference in the Hildebrand solubility parameter of the solvent system and the non-solvent system (e.g., $\delta_{solvent} - \delta_{non-solvent}$) is from about 1 to about 15 calories$^{1/2}$/cm$^{3/2}$, in some embodiments from about 4 to about 12 calories$^{1/2}$/cm$^{3/2}$, and in some embodiments, from about 6 to about 10 calories$^{1/2}$/cm$^{3/2}$. Within these ranges, the solvent/non-solvent will have enough miscibility to allow solvent extraction to occur, but not too miscible so that phase inversion could not be accomplished. Suitable solvents for use in the solvent system may include, for instance, water, saline, glycerol, etc., as well as combinations thereof. Likewise, suitable non-solvents for use in the non-solvent system may include acetone, n-propyl alcohol, ethyl alcohol, methanol, n-butyl alcohol, propylene glycol, ethylene glycol, etc., as well as combinations thereof.

Typically, the volume ratio of the solvent system to the non-solvent system ranges from about 50:1 to about 1:200 (volume per volume), in some embodiments from about 10:1 to about 1:180 (volume per volume), in some embodiments from about 1:1 to about 1:160 (volume per volume), in some embodiments from about 1:60 to about 1:150 (volume per volume), in some embodiments from about 1:1 to about 1:60 (volume per volume), and in some embodiments from about 1:1 to about 1:2 (volume per volume). After contact with the non-solvent and the phase inversion is completed, the liquid phase may be dried and/or removed using any suitable technique, such as by increased temperature, time, vacuum, and/or flow rate control using any suitable equipment (e.g., forced air ovens and vacuum ovens). In one example, for instance, high temperature drying at temperatures up to about 175° C. can leave up to about 16% wt. ethanol in the sample. The sample can then be placed in a humidity chamber at 69° C. at a 50% relative humidity to reduce the ethanol content to less than 0.13%.

II. Feminine Care Absorbent Article

The superabsorbent particles may be employed in a wide variety of different feminine care absorbent articles, such as sanitary napkins, pads, etc. The absorbent article typically contains an absorbent member (e.g., core layer, intake layer, etc.) positioned between a baffle and a topsheet.

The absorbent member may be formed from a single absorbent layer or a composite containing separate and distinct absorbent layers. Typically, however, the absorbent member contains the superabsorbent particles of the present invention, optionally in combination with a fibrous material. The absorbent member may, for example, contain a fibrous material in combination with the superabsorbent particles. The superabsorbent particles may, for instance, constitute from about 20 wt. % to about 90 wt. %, in some embodiments from about 30 wt. % to about 85 wt. %, and in some embodiments, from about 40 wt. % to about 80 wt. % based on a total weight of a layer of the absorbent member, while the fibrous material may constitute from about 10 wt. % to about 80 wt. %, in some embodiments from about 15 wt. % to about 70 wt. %, and in some embodiments, from about 20 wt. % to about 60 wt. % based on a total weight of a layer of the absorbent member. The superabsorbent particles can be substantially homogeneously mixed with the fibrous material or can be nonuniformly mixed. The superabsorbent particles can also be selectively placed into desired regions of the absorbent member, such as in the target zone for example, to better contain and absorb body exudates.

The fibrous material employed in the absorbent member may contain absorbent fibers, such as cellulosic fibers (e.g., pulp fibers). The cellulosic fibers may, for instance, include softwood pulp fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Hardwood fibers, such as eucalyptus, maple, birch, aspen, and so forth, can also be used. Synthetic polymer fibers (e.g., melt-spun thermoplastic fibers) may also be employed, such as meltblown fibers, spunbond fibers, etc. For instance, meltblown fibers may be employed that are formed from a thermoplastic polymer, such as a polyolefin, elastomer, etc. In certain embodiments, the fibrous material may also be a composite of different types of fibers, such as absorbent fibers and meltblown fibers. One example of such a composite is a "coform" material such as described in U.S. Pat. No. 4,100,324 to Anderson, et al.; U.S. Pat. No. 5,350,624 to Georger, et al.; and U.S. Pat. No. 5,508,102 to Georger, et al., as well as U.S. Patent Application Publication Nos. 2003/0200991 to Keck, et al. and 2007/0049153 to Dunbar, et al. The absorbent member can also include a laminate of fibrous webs and superabsorbent particles and/or a suitable matrix for maintaining the superabsorbent particles in a localized area.

Figure 7:
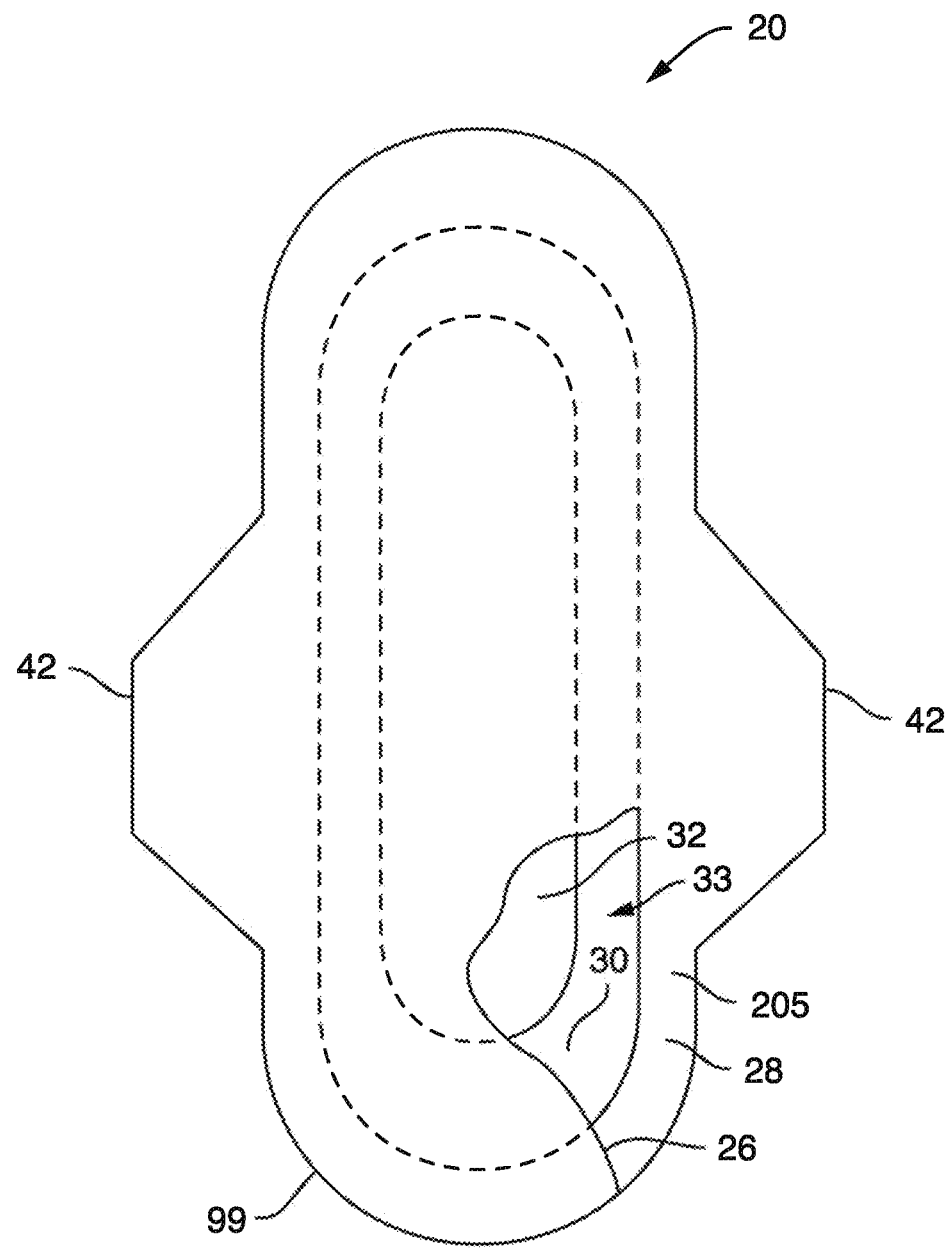
FIG. 7 is a perspective view of embodiment of a feminine care absorbent article of the present invention.

Referring to FIG. 7, for instance, one particular embodiment of a feminine care absorbent article 201 is shown. More particularly, the article 20 includes a topsheet 26, a baffle 28, and an absorbent member 33 positioned between the topsheet 26 and the baffle 28. The topsheet 26 defines a body-facing surface of the absorbent article 20. The absorbent member 33 is positioned inwardly from the outer periphery of the absorbent article 20 and includes a body-facing side positioned adjacent the topsheet 26 and a garment-facing surface positioned adjacent the baffle 28. Typically, the topsheet 26 and the baffle 28 are joined by adhesive bonding, ultrasonic bonding, or any other suitable joining method known in the art, the sealed edges defining an overall sealed peripheral edge 99 of the article 20. The article 20 may take on various geometries but will generally have opposite lateral sides and longitudinal ends.

The topsheet 26 helps provide comfort and conformability, and also helps direct bodily exudates away from the body toward the absorbent member 30. Typically, the topsheet 26 and the baffle 28 have peripheral margins 99 that extend outwardly beyond the terminal, peripheral edges of the absorbent member 30, and the extending margins are joined together to partially or entirely, surround or enclose the absorbent core. The topsheet 26 contacts the body of the user and is liquid-permeable. The topsheet 26 may be formed from one or multiple layers of materials. The liquid-permeable topsheet 26 has an outwardly facing surface that may contact the body of the wearer and receive fluids from the body. The topsheet 26 may define an inner region positioned between laterally spaced first and second outer regions. The inner and outer regions may be formed from a single section of material, or from multiple sections. Such multi-section topsheet configurations are known in the art and described in more detail, for instance, in U.S. Pat. No. 5,415,640 to Kirby, et al. Whether having one or multiple sections, the topsheet 26 may be made from any liquid-permeable material known in the art. For example, the topsheet 26 can be constructed of any woven or nonwoven material that is easily penetrated by bodily exudates. Examples of suitable materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. A specific example of a suitable topsheet material is a bonded carded web made of polypropylene and polyethylene, such as that used as topsheet stock for KOTEX® pantiliners. U.S. Pat. No. 4,801,494 to Datta, et al. and U.S. Pat. No. 4,908,026 to Sukiennik, et al. describe various other topsheet materials that may be used in the present invention. Such materials typically have a basis weight of less than about 100 gsm, and in some embodiments, from about 10 gsm to about 40 gsm.

The baffle 28 is generally liquid-impermeable and designed to face the inner surface, i.e., the crotch portion of an undergarment (not shown). The baffle 28 may permit a passage of air or vapor out of the absorbent article 20, while still blocking the passage of liquids. Any liquid-impermeable material may generally be utilized to form the baffle 28. For example, one suitable material that may be utilized is a microporous polymeric film, such as polyethylene or polypropylene. In particular embodiments, a polyethylene film is utilized that has a thickness in the range of about 0.2 mils to about 5.0 mils, and particularly between about 0.5 to about 3.0 mils. A specific example of a baffle material is a polyethylene film such as that used in KOTEX® pantiliners.

As indicated above, an absorbent member 33 is positioned between the topsheet 26 and the baffle 28 that provides capacity to absorb and retain bodily exudates. The absorbent member 33 may generally contain any number of layers desired. In one embodiment, for example, the absorbent member 33 contains an absorbent core 30. If desired, the absorbent core 30 may contain the superabsorbent particles of the present invention and optionally a fibrous material (e.g., absorbent fibers, synthetic polymer fibers, or a combination thereof), such as described above. In one embodiment, for instance, the absorbent core 33 may include one or more layers (e.g., two layers) of an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material includes a matrix of cellulosic fluff, and may also include the superabsorbent particles of the present invention. The cellulosic fluff may include a blend of wood pulp fluff. One suitable type of fluff is identified with the trade designation NB 416, available from Weyerhaeuser Corp., and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. A coform nonwoven material may also be employed. Methods and apparatus for carrying out such techniques are well known in the art.

Although not required, the absorbent member 33 may also contain other additional layers as is known in the art. In FIG. 7, for example, a liquid-permeable intake layer 32 is positioned between the topsheet 26 and the absorbent member 30. The intake layer 32 may be made of a material that is capable of rapidly transferring, in the z-direction, body fluid that is delivered to the topsheet 26. The intake layer 32 may generally have any shape and/or size desired. In one embodiment, the intake layer 32 has a generally ovular shape, with a length and/or width less than the overall length and/or width of the absorbent core 30. Any of a variety of different materials are capable of being used for the intake layer 32 to accomplish the above-mentioned functions. The material may be synthetic, cellulosic, or a combination of synthetic and cellulosic materials. For example, airlaid cellulosic tissues may be suitable for use in the intake layer 32. The airlaid cellulosic tissue may have a basis weight ranging from about 10 grams per square meter (gsm) to about 300 gsm, and in some embodiments, between about 40 gsm to about 150 gsm. The airlaid tissue may be formed from hardwood and/or softwood fibers. The airlaid tissue has a fine pore structure and provides an excellent wicking capacity, especially for menses.

The topsheet 26 may be maintained in secured relation with the absorbent member 30 by bonding all or a portion of the adjacent surfaces to one another. A variety of bonding mechanisms known to one of skill in the art may be utilized to achieve any such secured relation. Examples of such mechanisms include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent (e.g., ultrasonically fusing).

If desired, the feminine care absorbent article 20 may also include laterally extending wing portions 42 that may be integrally connected to side regions along the intermediate portion of the article. For example, the wing portions 42 may be separately provided members that are subsequently attached or otherwise operatively joined to the intermediate portion of the article. In other configurations, the wing portions may be unitarily formed with one or more components of the article.

As representatively shown in FIG. 7, for example, either or both wing portions 42 may be formed from a corresponding, operative extension of the material employed to form the baffle 28. Alternatively, either or both wing portions 42 may be formed from a corresponding, operative extension of the material employed to form the topsheet 26, or formed from a corresponding, operative combination of the topsheet and baffle materials.

The present invention may be better understood with reference to the following examples.

TEST METHODS

Pore Properties

The pore properties (e.g., total pore area, bulk density, pore size distribution, and percent porosity) of superabsorbent particles may be determined using mercury porosimetry (also known as mercury intrusion) as is well known in the art. For example, a commercially available porosiometer, such as AutoPore IV 9500 from Micrometrics, may be employed. Such devices generally characterize porosity by applying various levels of pressure to a sample immersed in mercury. The pressure required to intrude mercury into the sample's pores is inversely proportional to the size of the pores. Measurements may be performed at an initial pressure of 0.58 psi and at a final pressure of about 60,000 psi. The total pore area and bulk density may be directly measured during the mercury intrusion test. The overall pore size distribution may be derived from a graph of differential intrusion and pore diameter (μm). Likewise, the percent porosity may be calculated based on the reduction in bulk density reduction (assuming a constant size, packing, and shape of the particles) taking into consideration that approximately 50% of volume is occupied by empty space due to particles packing.

More particularly, the percent porosity may be determined according to the following equation:

$$100 \times 0.5 \times [(\text{Bulk Density of Control Sample} - \text{Bulk Density of Test Sample}) / \text{Bulk Density of Control Sample}]$$

wherein the Bulk Density (g/cm$^3$) is determined by mercury intrusion at a pressure of 0.58 psi.

Menses Simulant

For the tests described herein, a menses simulant is employed that contains defibrinated swine blood having a hematocrit level of 35 vol. % such as described in U.S. Pat. No. 5,888,231 to Achter, et al., which is incorporated herein in its entirety by reference thereto.

Absorbent Capacity (at 0.5 psi)

The saturated capacity of the superabsorbent measures the capacity of the superabsorbent particles to swell to the maximum possible capacity in the menses simulant. The saturated capacity is measured by placing 0.2±0.005 grams of the prescreened sample into a water-permeable bag that will contain the sample while allowing a test solution (menses simulant) to be freely absorbed by the sample. A heat-sealable tea bag material, such as model designation 1234T heat sealable filter paper, may be suitable. The bag is formed by folding a 5-inch by 3-inch sample of the bag material in half and heat-sealing two of the open edges to form a 2.5-inch by 3-inch rectangular pouch. The heat seals may be about 0.25 inches inside the edge of the material. After the sample is placed in the pouch, the remaining open edge of the pouch may also be heat-sealed. Empty bags may be made to serve as controls. Three samples (e.g., filled and sealed bags) are prepared for the test. The sealed bag with superabsorbent is placed in a trough containing menses simulant for 30 minutes to allow the superabsorbent particles to swell. The sealed bag with swollen superabsorbent particles is suspended for 5 minutes to allow any excess menses simulant that has not been absorbent by the superabsorbent particles to drip out of the sealed bag. The bag is then placed in vacuum box and pressure at 0.5 psi is applied for 5 minutes to the bag to drain out menses simulant that will be forced out of the swollen superabsorbent particles under pressure. The bag with swollen superabsorbent particles is then weighed and the absorbent capacity at 0.5 psi is measured in grams of menses simulant/gram of superabsorbent.

Saturated Capacity

The saturated capacity of the superabsorbent measures the capacity of the superabsorbent particles to swell to the maximum possible capacity in the menses simulant. The saturated capacity is measured by placing 0.2±0.005 grams of the prescreened sample into a water-permeable bag that will contain the sample while allowing a test solution (menses simulant) to be freely absorbed by the sample. A heat-sealable tea bag material, such as model designation 1234T heat sealable filter paper, may be suitable. The bag is formed by folding a 5-inch by 3-inch sample of the bag material in half and heat-sealing two of the open edges to form a 2.5-inch by 3-inch rectangular pouch. The heat seals may be about 0.25 inches inside the edge of the material. After the sample is placed in the pouch, the remaining open edge of the pouch may also be heat-sealed. Empty bags may be made to serve as controls. Three samples (e.g., filled and sealed bags) are prepared for the test. The sealed bag with superabsorbent is placed in a trough containing menses simulant for 30 minutes to allow the superabsorbent particles to swell. The sealed bag with swollen superabsorbent particles is suspended for 5 minutes to allow any excess menses simulant that has not been absorbent by the superabsorbent particles to drip out of the sealed bag. The bag with the swollen superabsorbent particles is weighed and the amount of menses simulant absorbed by the superabsorbent particles is calculated as grams of menses simulant/gram of superabsorbent.

Saturation Rate

The "Saturation Rate" of superabsorbent particles can be determined at a designated time interval by dividing the Saturated Capacity (g/g) described above by the specific time interval (kiloseconds, ks) of interest, such as 0.015, 0.030, 0.060, 0.120, 0.300, 0.600, 1.8, or 3.6 kiloseconds.

Centrifuge Retention Capacity (CRC)

The Centrifuge Retention Capacity (CRC) test measures the ability of superabsorbent particles to retain liquid after being saturated and subjected to centrifugation under controlled conditions. The resultant retention capacity is stated as grams of liquid retained per gram weight of the sample (g/g). The sample to be tested is prepared from particles that are prescreened through a U.S. standard 30-mesh screen and retained on a U.S. standard 50-mesh screen. The particles can be prescreened by hand or automatically and are stored in a sealed airtight container until testing. The retention capacity is measured by placing 0.2±0.005 grams of the prescreened sample into a water-permeable bag that will contain the sample while allowing a test solution (menses simulant) to be freely absorbed by the sample. A heatsealable tea bag material, such as model designation 1234T heatsealable filter paper, may be suitable. The bag is formed by folding a 5-inch by 3-inch sample of the bag material in half and heat-sealing two of the open edges to form a 2.5-inch by 3-inch rectangular pouch. The heat seals may be about 0.25 inches inside the edge of the material. After the sample is placed in the pouch, the remaining open edge of the pouch may also be heat-sealed. Empty bags may be made to serve as controls. Three samples (e.g., filled and sealed bags) are prepared for the test. The filled bags are tested within three minutes of preparation unless immediately placed in a sealed container, in which case the filled bags must be tested within thirty minutes of preparation.

The bags are placed between two TEFLON® coated fiberglass screens having 3-inch openings (Taconic Plastics, Inc., Petersburg, N.Y.) and submerged in a pan of the test solution at 23° C., making sure that the screens are held down until the bags are completely wetted. After wetting, the samples remain in the solution for about 30±1 minute, at which time they are removed from the solution and temporarily laid on a non-absorbent flat surface. For multiple tests, the pan should be emptied and refilled with fresh test solution after 24 bags have been saturated in the pan.

The wet bags are then placed into the basket of a suitable centrifuge capable of subjecting the samples to a g-force of about 350. One suitable centrifuge is a Heraeus LaboFuge 400 having a water collection basket, a digital rpm gauge, and a machined drainage basket adapted to hold and drain the bag samples. Where multiple samples are centrifuged, the samples may be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the samples. The amount of solution retained by the sample, taking into account the solution retained by the bag itself, is the centrifuge retention capacity (CRC) of the sample, expressed as grams of fluid per gram of sample. More particularly, the centrifuge retention capacity is determined as:

$$\frac{\text{Sample Bag Weight After Centrifuge} - \text{Empty Bag Weight After Centrifuge} - \text{Dry Sample Weight}}{\text{Dry Sample Weight}}$$

The three samples are tested and the results are averaged to determine the retention capacity (CRC) of the superabsorbent material. The samples are tested at 23° C. and 50% relative humidity.

Vortex Time

The Vortex Time is the amount of time in seconds required for a predetermined mass of superabsorbent particles to close a vortex created by stirring 50 milliliters of a menses simulant at 750 revolutions per minute on a magnetic stir plate. The time it takes for the vortex to close is an indication of the free swell absorbing rate of the particles. The vortex time test may be performed at a temperature is 23° C. and relative humidity of 50% according to the following procedure:
(1) Measure 50 milliliters (±0.01 milliliter) of a menses simulant into the 100-milliliter beaker.
(2) Place a 7.9 millimeters x 32 millimeters TEFLON® covered magnetic stir bar without rings (such as that commercially available under the trade designation SIP® brand single pack round stirring bars with removable pivot ring) into the beaker.
(3) Program a magnetic stir plate (such as that commercially available under the trade designation DATA-PLATE® Model #721) to 600 revolutions per minute.
(4) Place the beaker on the center of the magnetic stir plate such that the magnetic stir bar is activated. The bottom of the vortex should be near the top of the stir bar. The superabsorbent particles are pre-screened through a U.S. standard #30 mesh screen (0.595 millimeter openings) and retained on a U.S. standard #50 mesh screen (0.297 millimeter openings).
(5) Weigh out the required mass of the superabsorbent particles to be tested on weighing paper.
(6) While the menses simulant is being stirred, quickly pour the absorbent polymer to be tested into the simulant and start a stopwatch. The superabsorbent particles to be tested should be added to the simulant between the center of the vortex and the side of the beaker.
(7) Stop the stopwatch when the surface of the menses simulant becomes flat and record the time. The time, recorded in seconds, is reported as the vortex time.

EXAMPLE 1

15.00 grams of commercially available crosslinked polyacrylate superabsorbent particles were initially provided. The particles were formed in a manner as described in U.S. Pat. No. 8,742,023 to Fuiimura, et al. and had an initial Vortex Time of 106 seconds and CRC of about 25 g/g when tested with a menses simulant. The particles were swollen in excess of a good solvent (i.e., saline) for 60 minutes to reach equilibrium swelling capacity. Next, excess of saline was drained and interstitial liquid removed using a vacuum filtration technique. The vacuum filtration system was comprised of a Buchner funnel, moistened filter paper, Buchner flask, rubber bung and vacuum tubing. The swollen superabsorbent particles were then manually transferred into 1 kg of high purity ACS grade methanol under constant stirring in 2 L Pyrex beaker. Stirring was performed with a magnetic bar with dimensions: L=5 cm, D=0.9 cm and a rate of stirring of 800-1000 rpm. After 30 minutes, the solvent mixture was drained and another 1 kg of fresh methanol was added to superabsorbent particles. After 30 minutes, the solvent mixture was again drained and the superabsorbent particles were transferred to a Teflon Petri dish and dried for 1 hour in air forced oven at 85° C. Then, the superabsorbent particles were transferred into a vacuum oven to complete drying and remove residual methanol. Drying occurred at a temperature of 120-140° C. and pressure of 30 inHg for 4 hours. The dried superabsorbent particles were then adjusted using set of sieves with mesh size of 45-850 microns. Particles with a size of 300-600 microns in diameter were collected for further evaluation.

EXAMPLE 2

Particles were formed as described in Example 1, except that ACS grade 200 proof high purity ethanol was used during the solvent/non-solvent exchange step.

EXAMPLE 3

Particles were formed as described in Example 1, except that isopropyl alcohol was used during the solvent/non-solvent exchange step.

EXAMPLE 4

Particles were formed as described in Example 1, except that acetone was used during the solvent/non-solvent exchange step.

Various pore properties were also determined for Examples 1-4 using the test referend above. The pore size distribution for the samples is shown in FIGS. 2-6 and the results are set forth in the table below.

| Example | Total Pore Area, ($m^2/g$) | Bulk density at 0.58 PSI, ($g/cm^3$) | Pore size range, ($\mu m$) | Porosity, (%) |
|---|---|---|---|---|
| 1 | 18.5 | 0.3085 | 0.01-4 | 28 |
| 2 | 22.1 | 0.3983 | 0.01-1 | 22 |
| 3 | 16.4 | 0.5538 | 0.01-1 | 11 |
| 4 | 15.2 | 0.4356 | 0.01-4 | 19 |
| Control (prior to solvent exchange) | 1.7 | 0.7003 | <0.01 | — |

EXAMPLE 5

Particles were formed as described in Example 2 except that the particles were initially swollen in a 5 wt. % solution of sodium chloride.

EXAMPLE 6

Particles were formed as described in Example 2 except that the particles were initially swollen in a 10 wt. % solution of sodium chloride.

EXAMPLE 7

Particles were formed as described in Example 2 except that the particles were initially swollen in a 15 wt. % solution of sodium chloride.

EXAMPLE 8

Particles were formed as described in Example 2 except that the particles were initially swollen in a 20 wt. % solution of sodium chloride.

EXAMPLE 9

Particles were formed as described in Example 2 except that the particles were initially swollen in a 30 wt. % solution of ACS grade 200 proof high purity ethanol in di-ionized water.

EXAMPLE 10

Particles were formed as described in Example 2 except that the particles were initially swollen in a 40 wt. % solution of ACS grade 200 proof high purity ethanol in di-ionized water.

EXAMPLE 11

Particles were formed as described in Example 2 except that the particles were initially swollen in a 50 wt. % solution of ACS grade 200 proof high purity ethanol in di-ionized water.

EXAMPLE 12

Particles were formed as described in Example 2 except that the particles were initially swollen in a 60 wt. % solution of ACS grade 200 proof high purity ethanol in di-ionized water.

EXAMPLE 13

Particles were formed as described in Example 2 except that the particles were initially swollen in a 80 wt. % solution of ACS grade 200 proof high purity ethanol in di-ionized water.

EXAMPLE 14

Particles were formed as described in Example 1, except that the time of solvent/non-solvent exchange was reduced from 30 min to 15 min per step.

EXAMPLE 15

Particles were formed as described in Example 1, except that the time of solvent/non-solvent exchange was reduced from 30 min to 5 min per step.

EXAMPLE 16

Particles were formed as described in Example 1, except that the amount of methanol was reduced from 1 kg to 0.5 kg per step.

EXAMPLE 17

Particles were formed as described in Example 16, except that the time of solvent/poor solvent exchange was reduced from 30 minutes to 15 minutes.

EXAMPLE 18

Particles were formed as described in Example 16, except that the time of solvent/poor solvent exchange was reduced from 30 minutes to 5 minutes.

EXAMPLE 19

15.00 grams of the same superabsorbent particles provided in Example 1 were manually transferred into 1 kg of high purity ACS grade methanol under constant stirring in 2 L Pyrex beaker. Stirring was performed with a magnetic bar with dimensions: L=5 cm, D=0.9 cm and a rate of stirring of 800-1000 rpm. After 30 minutes, the solvent mixture was drained and another 1 kg of fresh methanol was added to superabsorbent particles. After 30 minutes, the solvent mixture was again drained and the superabsorbent particles were transferred to a Teflon Petri dish and dried for 1 hour in air forced oven at 85° C. Then, the superabsorbent particles were transferred into a vacuum oven to complete drying and remove residual methanol. Drying occurred at a temperature of 120-140° C. and pressure of 30 inHg for 4 hours. The dried superabsorbent particles were then adjusted using set of sieves with mesh size of 45-850 microns. Particles with a size of 300-600 microns in diameter were collected for further evaluation.

EXAMPLE 20

Particles were formed as described in Example 19, except that high purity ethanol was used to wash the superabsorbent particles.

EXAMPLE 21

Particles were formed as described in Example 19, except that high purity isopropyl alcohol was used to wash the superabsorbent particles.

EXAMPLE 22

Particles were formed as described in Example 19, except that high purity acetone was used to wash the superabsorbent particles.

Samples from of Example 20 were tested for vortex time, CRC, Absorbent Capacity (at 0.5 psi), and Saturated Capacity (1.8 ks) as discussed above. The results are set forth below.

| Example | Vortex Time (s) | Absorbent Capacity at 0.5 psi (g/g) | Saturated Capacity at 1.8 ks (g/g) | Saturation Rate (g/g/ks) |
|---|---|---|---|---|
| (Prior to Solvent Exchange) | 106 | 9 | 12.2 | 6 . . . 8 |
| After Solvent Exchange | 34 | 19 | 25.9 | 14.4 |

FIG. 1 also includes SEM microphotographs that show the particles of Example 1 before and after the solvent exchange procedure. As indicated, the solvent exchange resulting in particles containing a porous network that includes a plurality of nanopores.

EXAMPLE 23

Particles were formed in a manner as described in U.S. Pat. No. 8,742,023 to Fuiimura, et al. and tested with saline solution and had an initial Vortex Time of 35 seconds and CRC of about 27.5 g/g. The particles were sieved to 600-1,000 microns and then downsized using blender and sieved again to collect 300-600 microns.

EXAMPLE 24

Particles were formed in a manner as described in U.S. Pat. No. 8,742,023 to Fujimura, et al. and tested with saline solution and had an initial Vortex Time of 35 seconds and CRC of about 27.5 g/g. The particles were treated with a solvent and then washed with a non-solvent as described herein to create voided superabsorbent particles. The particles were then sieved to 600-850 microns and downsized using blender and sieved again to collect 300-600 microns.

Samples from Example 23 and Example 24 were tested for specific surface area (B.E.T.) in accordance with ISO 9277:2010. The results are set forth below.

| Example | B.E.T. Surface Area ($m^2/g$) |
|---|---|
| 23 | 0.16 |
| 24 | 2.43 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A feminine care absorbent article comprising an absorbent member positioned between a topsheet and a baffle, wherein the absorbent member contains at least one layer that comprises superabsorbent particles containing nanopores having an average cross-sectional dimension of from about 10 to about 500 nanometers, wherein the particles have a total pore area of greater than 2 $m^2/g$.

2. The feminine care absorbent article of claim 1, wherein the layer further contains a fibrous material, wherein the absorbent member comprises a fibrous material, wherein an average percent volume occupied by the nanopores within a given unit volume of the fibrous material is from 15% to 80% per cm3.

3. The feminine care absorbent article of claim 2, wherein the fibrous material includes absorbent fibers, synthetic polymer fibers, or a combination thereof.

4. The feminine care absorbent article of claim 3, wherein the absorbent fibers contain pulp fibers.

5. The feminine care absorbent article of claim 3, wherein the synthetic polymer fibers include meltblown fibers.

6. The feminine care absorbent article of claim 2, wherein the superabsorbent particles are mixed into a matrix of the fibrous material.

7. The feminine care absorbent article of claim 1, wherein the superabsorbent particles constitute from about 20 wt. % to about 90 wt. % of the layer of the absorbent member.

8. The feminine care absorbent article of claim 1, wherein the superabsorbent particles exhibit a Saturation Rate of about 7 g/g/ks or more after being placed into contact with a menses simulant for 1.8 kiloseconds.

9. The feminine care absorbent article of claim 1, wherein the percent porosity of the particles is greater than 5%, wherein the superabsorbent particles exhibit a Vortex Time of about 80 seconds or less.

10. The feminine care absorbent article of claim 1, wherein the superabsorbent particles exhibit an Absorbent Capacity at 0.5 psi (or 3.477 kPa) of about 15 g/g or more.

11. The feminine care absorbent article of claim 1, wherein the particles exhibit a Centrifuge Retention Capacity of about 20 g/g or more.

12. The feminine care absorbent article of claim 1, wherein the particles further contain micropores.

13. The feminine care absorbent article of claim 1, wherein the nanopores constitute at least about 25 vol. % of pores in the particles.

14. The feminine care absorbent article of claim 1, wherein the particles are formed from a crosslinked polymer that contains repeating units derived from one or more ethylenically unsaturated monomeric compounds having at least one hydrophilic radical.

15. The feminine care absorbent article of claim 14, wherein the monomeric compounds are monoethylenically unsaturated.

16. The feminine care absorbent article of claim 14, wherein the hydrophilic radical includes a carboxyl, carboxylic acid anhydride, carboxylic acid salt, sulfonic acid, sulfonic acid salt, hydroxyl, ether, amide, amino, quaternary ammonium salt group, or a combination thereof.

17. The feminine care absorbent article of claim 14 wherein the polymer contains repeating units derived from a (meth)acrylic acid monomeric compound or a salt thereof.

18. The feminine care absorbent article of claim 14, wherein the polymer contains an alkoxysilane functionality.

19. The feminine care absorbent article of claim 1, wherein the particles have a median size of from about 50 to about 2,000 micrometers.

20. The feminine care absorbent article of claim 1, wherein the particles have a specific surface area of about 0.2 square meters per gram or more as determined in accordance with ISO 9277:2010.

21. The feminine care absorbent article of claim 1, wherein the absorbent member contains an absorbent core that includes the superabsorbent particles.

22. The feminine care absorbent article of claim 21, wherein the absorbent member further contains an intake layer positioned adjacent to the absorbent core.

\* \* \* \* \*